United States Patent [19]

Okada et al.

[11] Patent Number: 4,950,668

[45] Date of Patent: Aug. 21, 1990

[54] PYRAZOLE DERIVATIVE, INSECTICIDAL OR MITICIDAL COMPOSITION CONTAINING THE SAME AS THE EFFECTIVE INGREDIENT

[75] Inventors: Itaru Okada, Shiroyama; Shuko Okui, Tokyo; Yoji Takahashi, Machida; Toshiki Fukuchi, Yokohama, all of Japan

[73] Assignee: Mitsubishi Kasei Corporation, Tokyo, Japan

[21] Appl. No.: 181,695

[22] Filed: Apr. 14, 1988

[30] Foreign Application Priority Data

Apr. 24, 1987 [JP] Japan ................. 62-101372

[51] Int. Cl.$^5$ .............. C07F 7/08; C07D 231/12; C07D 231/16; C07D 401/02
[52] U.S. Cl. .............. 514/232.2; 514/236.5; 514/316; 514/326; 514/406; 514/407; 544/80; 544/140; 546/14; 546/187; 546/211; 548/110; 548/373; 548/374; 548/375; 548/378
[58] Field of Search ............. 548/376, 377, 373, 378, 548/374, 110, 375; 514/406, 407, 232.2, 236.5, 326, 316; 544/140, 82; 546/211, 14, 187

[56] References Cited

U.S. PATENT DOCUMENTS

| | | | |
|---|---|---|---|
| 3,657,271 | 4/1972 | Swett ................. | 540/568 |
| 3,912,756 | 10/1975 | Wolff et al. ............ | 548/377 |
| 4,134,987 | 1/1979 | Huppatz ............... | 548/377 |
| 4,214,090 | 7/1980 | Huppatz ............... | 548/377 |
| 4,752,326 | 6/1988 | Ohyama et al. .......... | 71/92 |
| 4,772,309 | 9/1988 | Stetter et al. .......... | 544/140 |

FOREIGN PATENT DOCUMENTS

| | | |
|---|---|---|
| 508225 | 3/1980 | Australia . |
| 0200872 | 11/1986 | European Pat. Off. . |
| 0201852 | 11/1986 | European Pat. Off. . |
| 234119 | 10/1987 | European Pat. Off. . |
| 3633840 | 4/1988 | Fed. Rep. of Germany . |
| 57-106665 | 7/1982 | Japan . |
| 60-34949 | 2/1985 | Japan . |
| 62-120369 | 6/1987 | Japan . |

OTHER PUBLICATIONS

*Journal of Pharmaceutical Sciences,* 74, 1013–1015 (1985).
*Il Farmaco Ed. Sc.,* vol. 38, pp. 369–375, (1983).
*Farmaco Ed. Sci.,* 22(9), pp. 692–697 (1967).
*J. Med. Chem.,* vol. 27, 986–990 (1984).
*Synthesis,* 1981(9), pp. 727–729.

*Primary Examiner*—John M. Ford
*Assistant Examiner*—Catherine Scalzo
*Attorney, Agent, or Firm*—Oblon, Spivak, McClelland, Maier & Neustadt

[57] ABSTRACT

A novel pyrazole derivative and an insecticidal or miticidal composition containing the derivative as the effective ingredient are disclosed.

The pyrazole derivative of the present invention has an excellent controlling effect also against harmful insects and mites exhibiting resistance to conventional insecticides and does not disturb the ecosystem since it is less toxic and less residual.

7 Claims, No Drawings

PYRAZOLE DERIVATIVE, INSECTICIDAL OR MITICIDAL COMPOSITION CONTAINING THE SAME AS THE EFFECTIVE INGREDIENT

BACKGROUND OF THE INVENTION

The present invention relates to a novel pyrazole derivative, an insecticidal or miticidal composition containing the derivative as the effective ingredient and an exterminator for animal or plant parasiting mite.

Examples of the compounds having the structure similar to that of the present invention are described for those having fungicidal activity in Pest. Bio. Phy., 25, 163 (1986), Japanese Patent Laid-Open (KOKAI) No. 52-87168 and No. 60-34949; for those having herbicidal activity in Japanese Patent Laid-Open (KOKAI) No. 57-106665; and for those having medicinal properties in Japanese Patent Laid-Open (KOKAI) Nos. 47-6269, 48-56671, 52-83840, 56-73071 and 59-95272, Japanese Patent Publication No. 55-44751 and J. Pharm. Sci., 74, 1013 (1985). However, the insecticidal and miticidal activities of these compounds are not reported at all. Further, aralkyl group as the substituent for the nitrogen atom in the carbamoyl group or thiocarbamoyl group is not described at all the above-mentioned publications. While on the other hand, N-benzyl-3-methyl-5-pyrazole carboxamide and benzyl 3-methyl-5-pyrazole carboxylate are described in Farmaco, Ed. Sci., 22, 692 (1967). N-benzyl-1-(2,4-dinitrophenyl)-3-biphenyl-5-pyrazole carboxamide is disclosed in Rev. Roum. Chim., 23, 1581 (1978). Further, N-(4-hydroxybenzyl)-1,3-dimethyl-5-pyrazole carboxamide and N-(4-hydroxycarbonyl methoxybenzyl)-1,3-dimethyl-5-pyrazole carboxamide are disclosed in Japanese Patent Application Laid-Open (KOKAI) No. 50-58056. However, there are no report at all for the presence or absence of insecticidal and miticidal activities of these compounds.

Recently, harmful insects have acquired resistance to insecticides due to the long time use thereof and control by the conventional insecticides has become difficult. Harmful insects, for instance, resistive to typical insecticides such as organic phosphorus agent and carbamates have been developed generally and the control thereof is difficult. Further, it is also reported the development of harmful insects resistive to synthesized pyrethroide type insecticides noted in recent years. Aside from the above, some of organic phosphorus agent or carbamate agents show high toxicity and others disturb the ecosystem due to there high residual effect to bring about an extremely anxious problem. Accordingly, it has been expected to develop a novel insecticide showing excellent controlling effect even against those harmful insects and mites exhibiting resistance to the conventional insecticides and showing less toxicity and low residual effect.

The present inventors have made an earnest study for solving such a problem and have found a novel pyrazole derivative having excellent insecticidal or miticidal activity.

The present invention has been accomplished based on the findings.

SUMMARY OF THE INVENTION

In a first aspect of the present invention, there is provided a pyrazole derivative represented by the following formula (I):

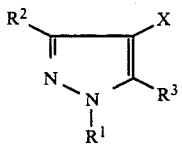

wherein $R^1$ represents $C_1$-$C_4$ alkyl group, $C_4$-$C_4$ haloalkyl group, phenyl group or benzyl group; one of $R^2$ and $R^3$ represents

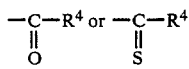

wherein $R^4$ represents

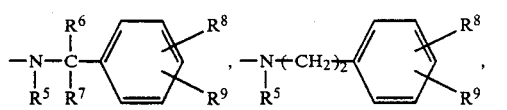

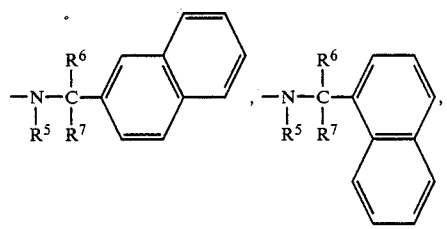

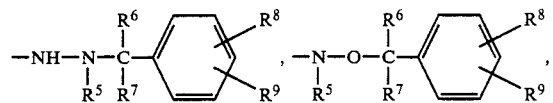

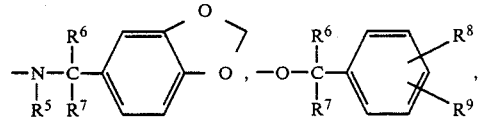

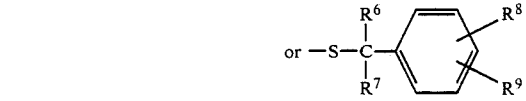

wherein $R^5$, $R^6$ and $R^7$ represent respectively hydrogen atom, $C_1$-$C_4$ alkyl group or phenyl group, $R^8$ and $R^9$ represent respectively hydrogen atom, halogen atom, $C_1$-$C_8$ alkyl group, $C_3$-$C_5$ alkenyl group, $C_3$-$C_5$ alkynyl group, $C_3$-$C_6$ cycloalkyl group, $C_2$-$C_4$ alkoxyalkyl group, $C_1$-$C_4$ alkoxy group, $C_1$-$C_4$ haloalkoxy group, nitro group, trifluoromethyl group, phenyl group, benzyl group, phenoxy group, benzyloxy group, amino group, $C_1$-$C_4$ alkylamino group, $C_2$-$C_8$ dialkylamino group, cyano group, carboxyl group, $C_2$-$C_5$ alkoxycarbonyl group, $C_4$-$C_7$ cycloalkoxycarbonyl group, $C_3$-$C_9$ alkoxyalkoxycarbonyl group, $C_2$-$C_6$ alkylaminocarbonyl group, $C_3$-$C_{11}$ dialkylaminocarbonyl group, piperidinocarbonyl group, morpholinocarbonyl group, trimethylsilyl group, $C_1$-$C_4$ alkylthio group, $C_1$-$C_4$ alkylsulfinyl group, or $C_1$-$C_4$ alkylsulfonyl group, the other of $R^2$ and $R^3$ represents hydrogen atom, $C_1$-$C_4$ alkyl group, $C_1$-$C_4$ haloalkyl group, $C_3$-$C_6$ cycloalkyl group or phenyl group; X represents hydrogen atom, halogen atom, $C_1-C_4$ alkyl group, nitro group, cyano group, $C_1-C_5$ alkylamino group, $C_2-C_{10}$ dialkylamino group and $C_2-C_7$ acylamino group.

In a second aspect of the present invention, there is provided an insecticidal or miticidal composition comprising an insecticidally or miticidally effective amount of a pyrazole derivative represented by the following formula (I):

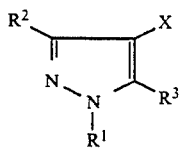
(I)

wherein $R^1$ represents $C_1-C_4$ alkyl group, $C_1-C_4$ haloalkyl group, phenyl group or benzyl group; one of $R^2$ and $R^3$ represents

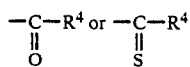

wherein $R^4$ represents

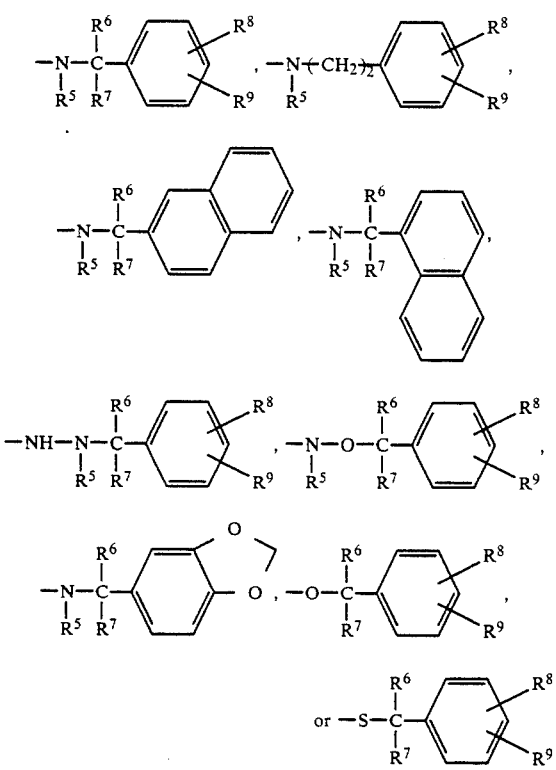

wherein $R^5$, $R^6$ and $R^7$ represent respectively hydrogen atom, $C_1-C_4$ alkyl group or phenyl group, $R^8$ and $R^9$ represent respectively hydrogen atom, halogen atom, $C_1-C_8$ alkyl group, $C_3-C_5$ alkenyl group, $C_3-C_5$ alkynyl group, $C_3-C_6$ cycloalkyl group, $C_2-C_4$ alkoxyalkyl group, $C_1-C_4$ alkoxy group, $C_1-C_4$ haloalkoxy group, nitro group, trifluoromethyl group, phenyl group, benzyl group, phenoxy group, benzyloxy group, amino group, $C_1-C_4$ alkylamino group, $C_2-C_8$ dialkylamino group, cyano group, carboxyl group, $C_2-C_5$ alkoxycarbonyl group, $C_4-C_7$ cycloalkoxycarbonyl group, $C_3-C_9$ alkoxyalkoxycarbonyl group, $C_2-C_6$ alkylaminocarbonyl group, $C_3-C_{11}$ dialkylaminocarbonyl group, piperidinocarbonyl group, morpholinocarbonyl group, trimethylsilyl group, $C_1-C_4$ alkylthio group, $C_1-C_4$ alkylsulfinyl group, or $C_1-C_4$ alkylsulfonyl group the other of $R^2$ and $R^3$ represents hydrogen atom, $C_1-C_4$ alkyl group, $C_1-C_4$ haloalkyl group, $C_3-C_6$ cycloalkyl group or phenyl group; X represents hydrogen atom, halogen atom, $C_1-C_4$ alkyl group, nitro group, cyano group, $C_1-C_5$ alkylamino group, $C_2-C_{10}$ dialkylamino group and $C_2-C_7$ acylamino group, and insecticidally and miticidally acceptable adjuvant(s).

In a third aspect of the present invention, there is provided a method of controlling insects and mites, which comprises applying an insecticidally and miticidally effective amount of a pyrazole derivative represented by the following formula (I):

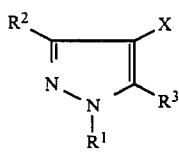
(I)

wherein $R^1$ represents $C_1-C_4$ alkyl group, $C_1-C_4$ haloalkyl group, phenyl group or benzyl group; one of $R^2$ and $R^3$ represents $$-\underset{\underset{O}{\|}}{C}-R^4 \text{ or } -\underset{\underset{S}{\|}}{C}-R^4$$

wherein $R^4$ represents wherein $R^5$, $R^6$ and $R^7$ represent respectively hydrogen atom, $C_1-C_4$ alkyl group or phenyl group, $R^8$ and $R^9$ represent respectively hydrogen atom, halogen atom, $C_1$–$C_8$ alkyl group, $C_3$–$C_5$ alkenyl group, $C_3$–$C_5$ alkynyl group, $C_3$–$C_6$ cycloalkyl group, $C_2$–$C_4$ alkoxyalkyl group, $C_1$–$C_4$ alkoxy group, $C_1$–$C_4$ haloalkoxy group, nitro group, trifluoromethyl group, phenyl group, benzyl group, phenoxy group, benzyloxy group, amino group, $C_1$–$C_4$ alkylamino group, $C_2$–$C_8$ dialkylamino group, cyano group, carboxyl group, $C_2$–$C_5$ alkoxycarbonyl group, $C_4$–$C_7$ cycloalkoxycarbonyl group, $C_3$–$C_9$ alkoxyalkoxycarbonyl group, $C_2$–$C_6$ alkylaminocarbonyl group, $C_3$–$C_{11}$ dialkylaminocarbonyl group, piperidinocarbonyl group, morpholinocarbonyl group, trimethylsilyl group, $C_1$–$C_4$ alkylthio group, $C_1$–$C_4$ alkylsulfinyl group, or $C_1$–$C_4$ alkylsulfonyl group the other of $R^2$ and $R^3$ represents hydrogen atom, $C_1$–$C_4$ alkyl group, $C_1$–$C_4$ haloalkyl group, $C_3$–$C_6$ cycloalkyl group or phenyl group; X represents hydrogen atom, halogen atom, $C_1$–$C_4$ alkyl group, nitro group, cyano group, $C_1$–$C_5$ alkylamino group, $C_2$–$C_{10}$ dialkylamino group and $C_2$–$C_7$ acylamino group, to eggs or larvae of said insects or mites.

In a fourth aspect of the present invention, there is provided a process for producing a pyrazole derivative represented by the following formula (I):

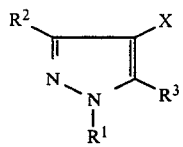

wherein $R^1$ represents $C_1$–$C_4$ alkyl group, $C_1$–$C_4$ haloalkyl group, phenyl group or benzyl group; one of $R^2$ and $R^3$ represents

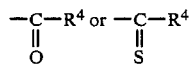

wherein $R^4$ represents

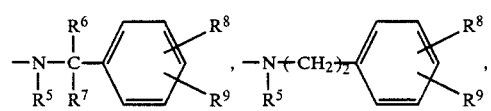

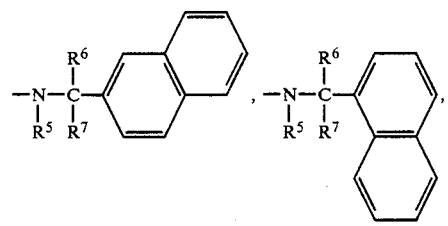

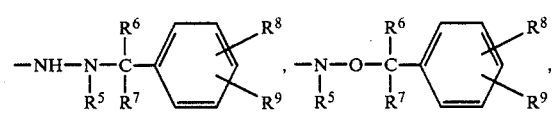

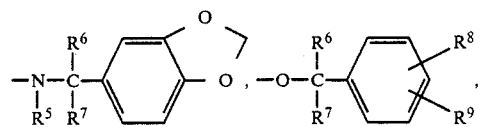

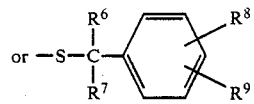

wherein $R^5$, $R^6$ and $R^7$ represent respectively hydrogen atom, $C_1$–$C_4$ alkyl group or phenyl group, $R^8$ and $R^9$ represent respectively hydrogen atom, halogen atom, $C_1$–$C_8$ alkyl group, $C_3$–$C_5$ alkenyl group, $C_3$–$C_5$ alkynyl group, $C_3$–$C_6$ cycloalkyl group, $C_2$–$C_4$ alkoxyalkyl group, $C_1$–$C_4$ alkoxy group, $C_1$–$C_4$ haloalkoxy group, nitro group, trifluoromethyl group, phenyl group, benzyl group, phenoxy group, benzyloxy group, amino group, $C_1$–$C_4$ alkylamino group, $C_2$–$C_8$ dialkylamino group, cyano group, carboxyl group, $C_2$–$C_5$ alkoxycarbonyl group, $C_4$–$C_7$ cycloalkoxycarbonyl group, $C_3$–$C_9$ alkoxyalkoxycarbonyl group, $C_2$–$C_6$ alkylaminocarbonyl group, $C_3$–$C_{11}$ dialkylaminocarbonyl group, piperidinocarbonyl group, morpholinocarbonyl group, trimethylsilyl group, $C_1$–$C_4$ alkylthio group, $C_1$–$C_4$ alkylsulfinyl group, or $C_1$–$C_4$ alkylsulfonyl group the other of $R^2$ and $R^3$ represents hydrogen atom, $C_1$–$C_4$ alkyl group, $C_1$–$C_4$ haloalkyl group, $C_3$–$C_6$ cycloalkyl group or phenyl group; X represents hydrogen atom, halogen atom, $C_1$–$C_4$ alkyl group, nitro group, cyano group, $C_1$–$C_5$ alkylamino group, $C_2$–$C_{10}$ dialkylamino group and $C_2$–$C_7$ acylamino group, which comprises reacting a compound represented by the following general formula (II):

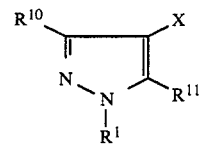

wherein $R^1$ and X have the same meanings as defined in the formula (I) described above, one of and $R^{10}$ and $R^{11}$ represents

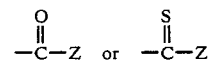

wherein Z represents chlorine atom, bromine atom, hydroxyl group, methoxy group, ethoxy group or propoxy group and the other of $R^{10}$ and $R^{11}$ represents a hydrogen atom, $C_1$–$C_4$ alkyl group, $C_1$–$C_4$ haloalkyl group, $C_3$–$C_6$ cycloalkyl group or phenyl group, with a compound represented by $R^4H$ wherein $R^4$ represents the same meanings as defined in the formula (I) described above.

DETAILED DESCRIPTION OF THE INVENTION

The present invention relates to a pyrazole derivative represented by the following formula (I)

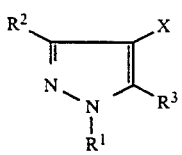

(I)

wherein $R^1$ represents $C_1$-$C_4$ alkyl group, $C_1$-$C_4$ haloalkyl group, phenyl group or benzyl group; one of $R^2$ and $R^3$ represents

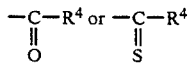

wherein $R^4$ represents

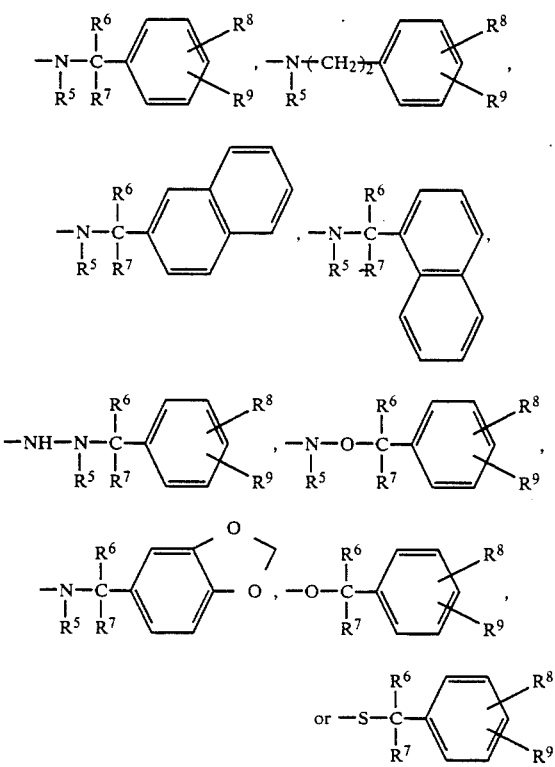

wherein $R^5$, $R^6$ and $R^7$ represent respectively hydrogen atom, $C_1$-$C_4$ alkyl group or phenyl group, $R^8$ and $R^9$ represent respectively hydrogen atom, halogen atom, $C_1$-$C_8$ alkyl group, $C_3$-$C_5$ alkenyl group, $C_3$-$C_5$ alkynyl group, $C_3$-$C_6$ cycloalkyl group, $C_2$-$C_4$ alkoxyalkyl group, $C_1$-$C_4$ alkoxy group, $C_1$-$C_4$ haloalkoxy group, nitro group, trifluoromethyl group, phenyl group, benzyl group, phenoxy group, benzyloxy group, amino group, $C_1$-$C_4$ alkylamino group, $C_2$-$C_8$ dialkylamino group, cyano group, carboxyl group, $C_2$-$C_5$ alkoxycarbonyl group, $C_4$-$C_7$ cycloalkoxycarbonyl group, $C_3$-$C_9$ alkoxyalkoxycarbonyl group, $C_2$-$C_6$ alkylaminocarbonyl group, $C_3$-$C_{11}$ dialkylaminocarbonyl group, piperidinocarbonyl group, morpholinocarbonyl group, trimethylsilyl group, $C_1$-$C_4$ alkylthio group, $C_1$-$C_4$ alkylsulfinyl group, or $C_1$-$C_4$ alkylsulfonyl group the other of $R^2$ and $R^3$ represents hydrogen atom, $C_1$-$C_4$ alkyl group, $C_1$-$C_4$ haloalkyl group, $C_3$-$C_6$ cycloalkyl group or phenyl group; X represents hydrogen atom, halogen atom, $C_1$-$C_4$ alkyl group, nitro group, cyano group, $C_1$-$C_5$ alkylamino group, $C_2$-$C_{10}$ dialkylamino group and $C_2$-$C_7$ acylamino group, as well as an insecticidal or miticidal composition containing the pyrazoles as the effective ingredient.

The present invention will be described more specifically.

In the formula (I), $R^1$ represents $C_1$-$C_4$ linear or branched alkyl group such as methyl group, ethyl group, n-propyl group, isopropyl group, n-butyl group, isobutyl group, sec-butyl group and t-butyl group; $C_1$-$C_4$ haloalkyl group such as chloromethyl group, bromomethyl group, 1-chloroethyl group, 2-chloroethyl group, 2-bromoethyl group, 3-bromopropyl group, 4-chlorobutyl group, difluoromethyl group and trifluoromethyl group; phenyl group; or benzyl group. Preferred $R^1$ is $C_1$-$C_4$ alkyl group, phenyl group or benzyl group, and more preferred $R^1$ is $C_1$-$C_4$ alkyl group.

One of $R^2$ and $R^3$ represents

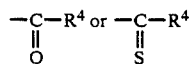

and the other of them represents hydrogen atom; $C_1$-$C_4$ linear or branched alkyl group such as methyl group, ethyl group, n-propyl group, isopropyl group, n-butyl group, isobutyl group, sec-butyl group and t-butyl group; $C_1$-$C_4$ haloalkyl group such as chloromethyl group, bromomethyl group, 1-chloroethyl group, 2-chloroethyl group, 2-bromoethyl group, 3-bromopropyl group, 4-chlorobutyl group, difluoromethyl group and trifluoromethyl group; $C_3$-$C_6$ cycloalkyl group such as cyclopropyl group, cyclobutyl group, cyclopentyl group and cyclohexyl group; or phenyl group.

It is preferable that $R^2$ represents hydrogen atom, $C_1$-$C_4$ alkyl group, $C_3$-$C_8$ cycloalkyl group or $C_1$-$C_4$ haloalkyl group and $R^3$ represents

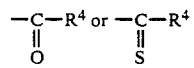

$R^4$ represents

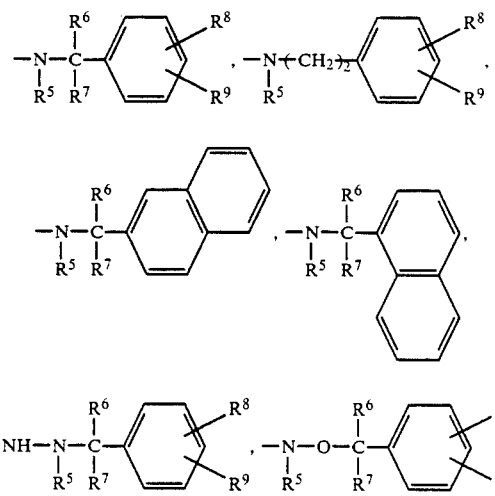

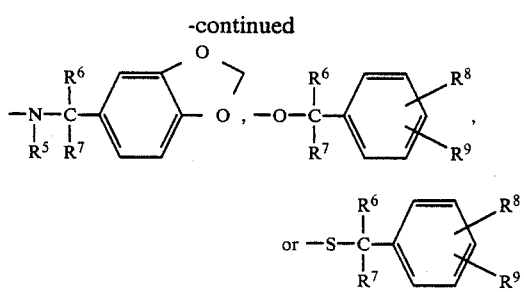

and, preferably, represents

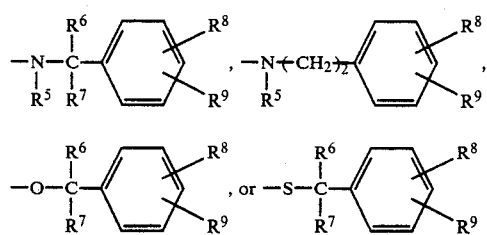

wherein $R^5$, $R^6$ and $R^7$ represent respectively hydrogen atom; $C_1$–$C_4$ linear or branched alkyl group such as methyl group, ethyl group, n-propyl group, isopropyl group, n-butyl group, isobutyl group, sec-butyl group and t-butyl group; or phenyl group. $R^8$ and $R^9$ represent respectively hydrogen atom; halogen atoms such as fluorine atom, chlorine atom, bromine atom and iodine atom; $C_1$–$C_8$ linear or branched alkyl group such as methyl group, ethyl group, n-propyl group, isopropyl group, n-butyl group, isobutyl group, sec-butyl group, t-butyl group, n-amyl group, isoamyl group, t-pentyl group, n-hexyl group, 1-ethyl-1-methylpropyl group and n-octyl group; $C_3$–$C_5$ alkenyl group such as allyl group, methallyl group and 2-butenyl group; $C_3$–$C_5$ alkynyl group such as propargyl group; $C_3$–$C_6$ cycloalkyl group such as cyclopropyl group, cyclobutyl group, cyclopentyl group and cyclohexyl group; $C_2$–$C_4$ alkoxyalkyl group such as ethoxymethyl group and ethoxyethyl group; $C_1$–$C_4$ linear or branched alkoxy group such as methoxy group, ethoxy group, n-propoxy group, isopropoxy group, n-butoxy group, isobutoxy group, sec-butoxy group and t-butoxy group; $C_1$–$C_4$ haloalkoxy group such as monofluoromethoxy group, difluoromethoxy group, trifluoromethoxy group, 2,2,2-trifluoroethoxy group, chloromethoxy group, 2-chloroethoxy group, 2-bromoethoxy group, 3-chloropropoxy group, 4-chlorobutoxy group, 4-bromobutoxy group and 1,1-dimethyl-2-chloroethoxy group; nitro group; trifluoromethyl group; phenyl group; benzyl group; phenoxy group; benzyloxy group; amino group; $C_1$–$C_4$ linear or branched alkylamino group such as methylamino group, ethylamino group, n-propylamino group, isopropylamino group, n-butylamino group, isobutylamino group, sec-butylamino group and t-butylamino group; $C_2$–$C_8$ di(linear or branched) alkylamino group such as dimethylamino group, diethylamino group, di-n-propylamino group, diisopropylamino group, di-n-butylamino group, diisobutylamino group, N-ethylmethylamino group, N-methylpropylamino group, N-n-butylethylamino group and N-isobutylethylamino group; cyano group; carboxyl group; $C_2$–$C_5$ linear or branched alkoxycarbonyl group such as methoxycarbonyl group, ethoxycarbonyl group, n-propoxycarbonyl group, isopropoxycarbonyl group, n-butoxycarbonyl group, isobutoxycarbonyl group, sec-butoxycarbonyl group and t-butoxycarbonyl group; $C_4$–$C_7$ cycloalkoxycarbonyl group such as cyclopropoxycarbonyl group, cyclobutoxycarbonyl group, cyclopentyloxycarbonyl group and cyclohexyloxycarbonyl group; $C_3$–$C_9$ alkoxyalkoxycarbonyl group such as methoxymethoxycarbonyl group, methoxyethoxycarbonyl group, methoxypropoxycarbonyl group, methoxybutoxycarbonyl group, ethoxyethoxycarbonyl group, n-propoxyethoxycarbonyl group, isopropoxyethoxycarbonyl group, n-(iso-, sec- or t-)butoxyethoxycarbonyl group and hexyloxyethoxycarbonyl group; $C_2$–$C_6$ alkylaminocarbonyl group such as methylaminocarbonyl group, ethylaminocarbonyl group, n-propylaminocarbonyl group, isopropylaminocarbonyl group, n-(iso-, sec- or t-)butylaminocarbonyl group, pentylaminocarbonyl group and hexylaminocarbonyl group; $C_3$–$C_{11}$ dialkylaminocarbonyl group such as dimethylaminocarbonyl group, diethylaminocarbonyl group, dipropylaminocarbonyl group, dibutylaminocarbonyl group, dipentylaminocarbonyl group, methylethylaminocarbonyl group, methylpropylaminocarbonyl group and ethylbutylaminocarbonyl group; piperidinocarbonyl group; morpholinocarbonyl group; trimethylsilyl group; $C_1$–$C_4$ linear or branched alkylthio group such as methylthio group, ethylthio group, n-propylthio group, isopropylthio group, n-butylthio group, isobutylthio group, sec-butylthio group and t-butylthio group; $C_1$–$C_4$ linear or branched alkylsulfinyl group such as methylsulfinyl group, ethylsulfinyl group, n-propylsulfinyl group, isopropylsulfinyl group, n-butylsulfinyl group, isobutylsulfinyl group, sec-butylsulfinyl group and t-butylsulfinyl group; or $C_1$–$C_4$ linear or branched alkylsulfonyl group such as methylsulfonyl group, ethylsulfonyl group, n-propylsulfonyl group, isopropylsulfonyl group, n-butylsulfonyl group, isobutylsulfonyl group, sec-butylsulfonyl group and t-butylsulfonyl group. Preferably, $R^5$ and $R^9$ represent hydrogen atom.

X represents hydrogen atom; halogen atom such as fluorine atom, chlorine atom, bromine atom and iodine atom; $C_1$–$C_4$ linear or branched alkyl group such as methyl group, ethyl group, n-propyl group, isopropyl group, n-butyl group, isobutyl group, sec-butyl group and t-butyl group; nitro group; cyano group; $C_1$–$C_5$ alkylamino group such as methylamino group, ethylamino group, n-propylamino group, isopropylamino group, n-butylamino group, isobutylamino group, sec-butylamino group, t-butylamino group and pentylamino group; $C_2$–$C_{10}$ dialkylamino group such as dimethylamino group, diethylamino group, dipropylamino group, dibutylamino group, dipentylamino group, methylethylamino group, methylpropylamino group and ethylbutylamino group; $C_2$–$C_7$ acylamino group such as acetylamino group, chloroacetylamino group, ethoxycarbonylamino group, benzoylamino group and propionylamino group. Among these, hydrogen atom, halogen atom, $C_1$–$C_4$ alkyl group, cyano group and $C_1$–$C_4$ alkylamino group are preferable.

Description is to be made for the production process of the compound according to the present invention.

The compound according to the present invention represented by the formula (I) described above can be produced in accordance with the following reaction scheme.

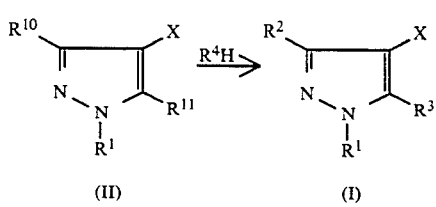

wherein $R^1$, $R^2$, $R^3$ and $R^4$ and X have the same meanings as defined in the formula (I) described above, one of $R^{10}$ and $R^{11}$ represents

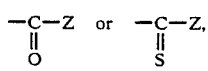

wherein Z represents chlorine atom, bromine atom, hydroxyl group, methoxy group, ethoxy group or propoxy group, and the other of them represents hydrogen atom, $C_1$-$C_4$ alkyl group, $C_1$-$C_4$ haloalkyl group, $C_3$-$C_6$ cycloalkyl group or phenyl group.

In a case where Z represents chlorine atom or bromine atom in the formula (II) described above, the compound of the formula (I) can be obtained by reacting the compound represented by the formula (II) with $R^4H$ in an aromatic hydrocarbon such as benzene, toluene and xylene; ketone such as acetone, methyl ethyl ketone and methyl isobutyl ketone; halogenated hydrocarbon such as chloroform and methylene chloride; water; esters such as methyl acetate, ethyl acetate; polar solvent such as tetrahydrofuran, acetonitrile, dioxane, N,N-dimethylformamide, N-methylpyrrolidone and dimethyl sulfoxide at a temperature from 0° to 30° C., preferably, from 0° to 5° C. under the presence of a base. The base can include sodium hydroxide, potassium hydroxide, sodium carbonate, potassium carbonate, pyridine and triethylamine.

Further, in a case where Z represents hydroxyl group, methoxy group, ethoxy group or propoxy group in the formula (II), the compound of the formula (I) can be obtained by reacting the compound of the formula (II) with $R^4H$ without using solvent or in a high boiling point solvent such as N,N-dimethylformamide, N-methylpyrrolidone and dimethyl sulfoxide at a temperature from 150° to 250° C., preferably from 200° to 250° C.

The compound represented by the formula (II) described above can be prepared, for example, according to the method as described in Bull. Soc. Chim. France, 293 (1966).

The compound represented by the formula (I) has a remarkable controlling activity against eggs and larvae of insects such as of Celeoptera, Lepidoptera, Hemiptera, Orthoptera and Diptera, as well as eggs and larvae of animal or plant parasiting spider mite. However, harmful insects against which the compound represented by the formula (I) shows a remarkable controlling activity are not restricted to those exemplified below.

1. Hemiptera

Delphacidae such as *Sogatella furcifera, Nilaparvata lugens, Laodelphax striatellus*, etc.; Leaf hopper such as *Nephotettix cincticeps*, etc.; Aphis such as *Myzus persicae*, etc.

2. Lepidoptera

*Spodoptera litura, Chilo suppressalis, Cnaphalocrosis medinalis*, etc.

3. Coleoptera

*Callosobruchus chinensis*, etc.

4. Diptera

*Musca domestica, Aedes aegypti, Culex pipiens molestus*, etc.

5. Spider mite

*Tetranychus urticae, Tetranychus cinnabarinus, Panonychus citri*, etc.

6. Tick

*Boophilus* spp., *Ornithodoros* spp., etc.

In the case of using the compound represented by the formula (I) according to the present invention as an insecticide or miticide, it may be used alone or usually formulated into emulsifiable concentrate, dust, wettable powder, solution, etc. together with adjuvants in the same manner as conventional agricultural chemicals and then used without or after dilution. The adjuvants are those used ordinarily for the formulation of the insecticides. For instance, there can be mentioned solid carrier such as talc, kaolin, diatomaceous earth, clay and starch; water; hydrocarbons such as cyclohexane, benzene, xylene and toluene; halogenated hydrocarbons such as chlorobenzene; ethers; amides such as dimethylformamide; ketones; alcohols; nitriles such as acetonitrile, as well as other known surface active agents such as emulsifiers and dispersing agents.

If desired, it is also possible to use in admixture or combination with other insecticides, miticides, fungicides, insect growth controlling agent, plant growth controlling agent, etc. Although the concentration for the effective ingredient in the formulated insecticidal or miticidal composition has no particular restrictions, it is usually contained from 0.5 to 20% by weight, preferably, from 1 to 10% by weight in dust; from 1 to 90% by weight, preferably, from 10 to 80% by weight in wettable powder; and from 1 to 90% by weight, preferably, from 10 to 40% by weight in emulsifiable concentrate.

In the case of using the compound represented by the formula (I) as the insecticide or miticide, it is usually used within the range of concentration of the active ingredient from 5 to 1000 ppm, preferably, from 10 to 500 ppm.

The present invention will be explained more specifically referring to the following preparation examples, formulation examples and test examples for the compound according to the present invention, but it should be understood that the present invention is not restricted only to the following examples.

EXAMPLE 1:

Preparation of N-(4-tert-butyl-α-methylbenzyl)-4-bromo-1,3-dimethyl-5-pyrazole carboxamide A mixture of 2.19 g of 4-bromo-1,3-dimethylpyrazole-5-carboxylic acid and 11.7 g of thionyl chloride was heated under reflux for one hour. After distilling off thionyl chloride under a reduced pressure, the residue was dissolved into 20 ml of toluene. The solution was dropped into 25 ml of a toluene solution containing 2.12 g of 4-tert-butyl-α-methylbenzylamine and 1.21 g of triethylamine at a temperature from 0 to 10° C. After dropping was over, the solution was stirred for 2 hours, poured into ice-water and extracted with toluene. The toluene layer was washed with an aqueous solution of sodium carbonate, water and then saturated aqueous solution of sodium chloride. After drying over anhydrous sodium sulfate, it was concentrated under a reduced pressure The residue was purified by silica gel column chromatography to obtain 3.41 g of the compound (No 13) described in Table 1.

NMR and IR for the compound were as described below.

$^1$HNMR(CDCl$_3$)δppm; 1.30 (s, 9H), 1.60 (d, 3H), 2.25 (s, 3H), 4.10 (s, 3H), 5.25 (m, 1H), 7.00 (b, 1H), 7.35 (m, 4H)

IR(KBr) cm$^{-1}$; 3330, 2970, 1640, 1535, 1290, 1270, 1035, 825, 570.

EXAMPLE 2

Preparation of N-(4-tert-butylbenzyl)-4-chloro-1,3-dimethyl-5-pyrazole carboxamide A mixture of 2.03 g of ethyl 4-chloro-1,3-dimethyl-pyrazole-5-carboxylate and 2.45 g of 4-tertbutylbenzylamine was heated at 200° C. for 4 hours under stirring. After cooling to room temperature, the reaction product was purified by silica gel column chromatography to obtain 2.24 g of the compound (No. 36) described in Table 1.

NMR and IR for the compound were as described below.

1HNMR(CDCl$_3$)δppm; 1.30 (s, 9H), 2.25 (s, 3H), 4.15 (s, 3H), 4.60 (d, 2H), 7.00 (b, 1H), 7.40 (m, 4H).

IR(KBr) cm$^{-1}$; 3300, 2960, 1650, 1560, 1465, 1300, 1090, 990, 820, 660, 640.

EXAMPLE 3

The compounds as described in Tables 1 to 3 were obtained according to the methods of Example 1 or 2.

TABLE 1

| Compound No. | R$^1$ | R$^2$ | R$^4$ | X | n$_D$ (Refractive index) m.p (Melting point) °C. |
|---|---|---|---|---|---|
| 1 | CH$_3$ | CH$_3$ | NH—CH(CH$_3$)—C$_6$H$_4$—C$_4$H$_9^t$ | H | 125.5–127.5 |
| 2 | " | " | NH—CH$_2$—C$_6$H$_5$ | Br | 117.0–118.0 |
| 3 | " | " | NH—CH(CH$_3$)—C$_6$H$_5$ | " | 103.5–105.5 |
| 4 | " | " | NH—C(CH$_3$)$_2$—C$_6$H$_5$ | " | 63.0–64.0 |
| 5 | " | " | NH—CH$_2$—C$_6$H$_4$(2-F) | " | 120.0–121.0 |
| 6 | " | " | NH—CH$_2$—C$_6$H$_4$—F | " | 135.5–136.5 |

TABLE 1-continued
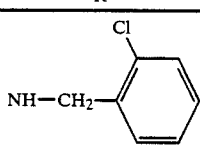
| Compound No. | R¹ | R² | R⁴ | X | $n_D$ (Refractive index) m.p (Melting point) °C. |
|---|---|---|---|---|---|
| 7 | " | " | 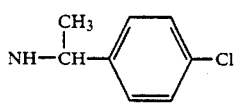 | " | 137.0–138.5 |
| 8 | " | " | 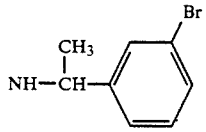 | " | 121.5–123.0 |
| 9 | " | " | 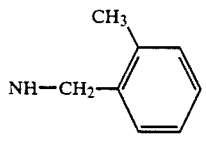 | " | 77.5–80.5 |
| 10 | " | " | 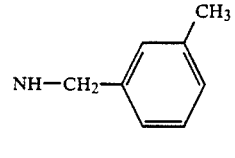 | " | 129.0–130.0 |
| 11 | " | " | 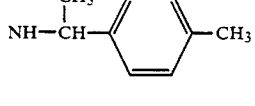 | " | 107.5–108.5 |
| 12 | " | " | 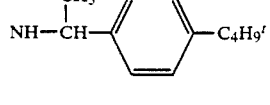 | " | 93.0–94.5 |
| 13 | " | " | 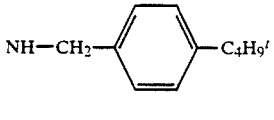 | " | 104.0–105.5 |
| 14 | " | " | 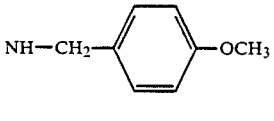 | " | 90.0–91.0 |
| 15 | " | " | 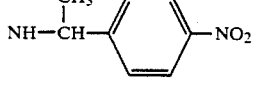 | " | 116.0–117.0 |
| 16 | " | " | 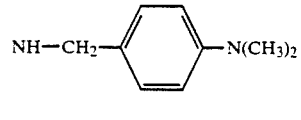 | " | 146.5–148.5 |
| 17 | " | " | NH—CH₂—⟨C₆H₄⟩—N(CH₃)₂ | " | 110.5–111.5 |

TABLE 1-continued
$$\underset{\underset{R^1}{N}}{\overset{R^2}{\underset{N}{\bigwedge}}}\overset{X}{\underset{C-R^4}{\bigvee}}\overset{}{\underset{O}{\parallel}}$$
| Compound No. | R¹ | R² | R⁴ | X | n_D (Refractive index) m.p (Melting point) °C. |
|---|---|---|---|---|---|
| 18 | " | " | 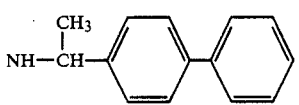 | " | 131.0–133.0 |
| 19 | " | " | 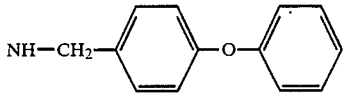 | " | 118.0–119.0 |
| 20 | " | " | 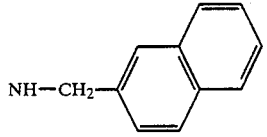 | " | 157.5–159.0 |
| 21 | " | " | 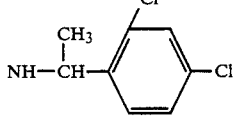 | " | 146.5–149.0 |
| 22 | " | " | 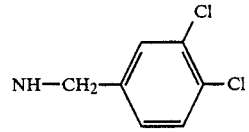 | " | 151.0–152.0 |
| 23 | " | " | 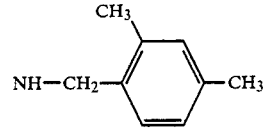 | " | 138.0–139.0 |
| 24 | " | " | 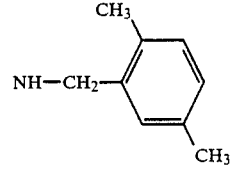 | " | 138.5–141.0 |
| 25 | " | " | 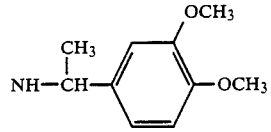 | " | 129.0–131.0 |
| 26 | " | " | 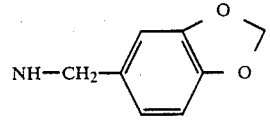 | " | 132.0–133.0 |

TABLE 1-continued

[Structure: pyrazole with R² at 3-position, X at 4-position, C(=O)-R⁴ at 5-position, N1-R¹]

| Compound No. | R¹ | R² | R⁴ | X | $n_D$ (Refractive index) m.p (Melting point) °C. |
|---|---|---|---|---|---|
| 27 | " | " | NH–CH(C₆H₅)₂ (benzhydrylamino) | " | 113.5–115.0 |
| 28 | " | " | N(CH₃)–CH₂–C₆H₅ | " | $n_D^{25}$ 1.5688 |
| 29 | " | " | NH–(CH₂)₂–C₆H₅ | " | 101.5–102.5 |
| 30 | " | " | O–CH(CH₃)–C₆H₄–$C_4H_9^t$ (4-) | " | $n_D^{24}$ 1.5428 |
| 31 | " | " | O–CH₂–C₆H₄–$C_4H_9^t$ (4-) | " | 59.0–59.5 |
| 32 | " | " | O–CH₂–C₆H₄–O–C₆H₅ (3-phenoxy) | " | $n_D^{24}$ 1.9952 |
| 33 | " | " | NH–CH₂–C₆H₄–$C_3H_7^i$ (4-) | Cl | 75.5–76.0 |
| 34 | " | " | NH–CH₂–C₆H₄–$C_4H_9^n$ (4-) | " | 72.0–73.5 |
| 35 | " | " | NH–CH(CH₃)–C₆H₄–$C_4H_9^t$ (4-) | " | 91.0–93.0 |
| 36 | " | " | NH–CH₂–C₆H₄–$C_4H_9^t$ (4-) | " | 78.0–79.0 |

TABLE 1-continued

R² on pyrazole C, X on pyrazole C, C(=O)R⁴ on pyrazole C, R¹ on N

| Compound No. | R¹ | R² | R⁴ | X | n_D (Refractive index) m.p (Melting point) °C. |
|---|---|---|---|---|---|
| 37 | " | " | NH–CH₂–C₆H₄(2-CF₃) | " | 127.5–128.5 |
| 38 | " | " | NH–CH₂–C₆H₄(3-CF₃) | " | 107.0–108.0 |
| 39 | " | " | NH–CH₂–C₆H₄(4-CF₃) | " | 102.0–103.0 |
| 40 | " | " | NH–CH₂–C₆H₄(4-OCH₃) | " | 100.0–101.0 |
| 41 | " | " | NH–CH₂–C₆H₄(4-$C_4H_9^t$) | CH₃ | 121.5–123.0 |
| 42 | H | " | NH–CH(CH₃)–C₆H₄(4-$C_4H_9^t$) | Br | 170.0–173.0 |
| 43 | C₂H₅ | " | NHCH₂–C₆H₄(4-$C_4H_9^t$) | Cl | 115.0–116.5 |
| 44 | $C_3H_7^i$ | " | " | " | 110.0–111.0 |
| 45 | $C_4H_9^n$ | " | " | " | 86.0–87.0 |
| 46 | $C_4H_9^t$ | " | NH–CH(CH₃)–C₆H₄(4-$C_4H_9^t$) | Br | 155.0–157.0 |
| 47 | C₆H₅ | " | NH–CH(CH₃)–C₆H₅ | " | 182.0–183.0 |
| 48 | " | " | NH–C(CH₃)₂–C₆H₅ | " | 148.5–150.0 |

TABLE 1-continued

Structure:
$$R^2\text{-pyrazole with }R^1\text{ on N1, }X\text{ at 4-position, }C(=O)R^4\text{ at 5-position}$$

| Compound No. | R¹ | R² | R⁴ | X | $n_D$ (Refractive index) m.p (Melting point) °C. |
|---|---|---|---|---|---|
| 49 | " | " | NH–CH$_2$–C$_6$H$_4$–C$_4$H$_9^t$ | Cl | 120.5–121.5 |
| 50 | CH$_2$–C$_6$H$_5$ | " | " | " | 91.0–93.0 |
| 51 | CH$_3$ | C$_2$H$_5$ | " | " | 61.0–62.0 |
| 52 | " | C$_3$H$_7^i$ | " | " | 64.0–66.0 |
| 53 | " | C$_4$H$_9^n$ | NH–CH$_2$–C$_6$H$_4$–C$_4$H$_9^t$ | " | 63.0–64.0 |
| 54 | " | C$_4$H$_9^i$ | " | " | 78.0–80.0 |
| 55 | " | C$_4$H$_9^t$ | NH–CH(CH$_3$)–C$_6$H$_5$ | Br | 82.5–85.5 |
| 56 | " | " | NH–C(CH$_3$)$_2$–C$_6$H$_5$ | " | 93.5–95.0 |
| 57 | " | " | NH–CH(CH$_3$)–C$_6$H$_4$–C$_4$H$_9^t$ | " | 86.5–87.5 |
| 58 | " | C$_6$H$_5$ | NH–CH$_2$–C$_6$H$_4$–C$_4$H$_9^t$ | Cl | 78.0–79.5 |
| 59 | " | CH$_3$ | NHCH$_2$–C$_6$H$_4$–C$_4$H$_9^{sec}$ | " | $n_D^{25}$ 1.5501 |
| 60 | " | " | NHCH$_2$–C$_6$H$_4$–C$_4$H$_9^i$ | " | 87.5–88.5 |
| 61 | " | " | NHCH$_2$–C$_6$H$_4$–C$_6$H$_{11}$ | " | 92.0–94.5 |
| 62 | " | " | N(CH$_3$)–CH$_2$–C$_6$H$_4$–C$_4$H$_9^t$ | " | 67.0–69.0 |

TABLE 1-continued

Structure:

$$\begin{array}{c} R^2 \quad X \\ \diagdown \quad / \\ N \quad C-R^4 \\ | \quad \| \\ R^1 \quad O \end{array}$$

(pyrazole with $R^2$ at 3-position, $X$ at 4-position, $C(=O)R^4$ at 5-position, $R^1$ on N1)

| Compound No. | $R^1$ | $R^2$ | $R^4$ | X | $n_D$ (Refractive index) m.p (Melting point) °C. |
|---|---|---|---|---|---|
| 63 | " | | NH–CH($C_3H_7^i$)–C6H5 | | 79.5–80.5 |
| 64 | " | " | NHCH2CH2–C6H4–4-Cl | " | 101.0–103.0 |
| 65 | " | " | NH–CH2CH2–C6H4–4-CH3 | " | 69.0–71.0 |
| 66 | " | " | NHCH2–C6H4–4-$OC_3H_7^i$ | " | 68.0–69.0 |
| 67 | " | " | NHCH2–C6H4–4-$SO_2CH_3$ | " | 76.0–78.0 |
| 68 | " | " | NHCH2–C6H4–4-$OCH_2C_6H_5$ | " | 88.0–90.0 |
| 69 | " | " | NHCH2–C6H4–4-$C_4H_9^t$ | $CH_3$ | 173–174 |
| 70 | " | $C_2H_5$ | " | H | 153–155 |
| 71 | " | " | " | Cl | 167–169 |
| 72 | $CH_3$ | H | " | " | 64–66 |
| 73 | " | " | NHCH2–C6H4–4-$C_4H_9^n$ | " | 86–87 |
| 74 | " | " | NHCH2–C6H4–4-C($CH_3$)2$CH_2CH_3$ | " | 70–71 |
| 75 | " | $CH_3$ | NHCH2–C6H4–4-$C_4H_9^t$ | H | 111–112.5 |
| 76 | " | " | $SCH_2$–C6H5 | Cl | 88–90 |

TABLE 1-continued $$\underset{R^1}{\underset{N-N}{R^2}}\underset{C-R^4}{\overset{X}{\underset{\parallel}{\bigg|}}}$$

| Compound No. | R$^1$ | R$^2$ | R$^4$ | X | n$_D$ (Refractive index) m.p (Melting point) °C. |
|---|---|---|---|---|---|
| 77 | " | " | SCH$_2$—C$_6$H$_4$—C$_4$H$_9^t$ | " | 65–66 |
| 78 | " | " | NHNHCH$_2$—C$_6$H$_4$—C$_4$H$_9^t$ | " | 71.5–73.5 |
| 79 | " | " | NHCH$_2$—C$_6$H$_4$—C$_4$H$_9^t$ | CN | 95–96.5 |
| 80 | " | " | " | NO$_2$ | 145–147 |
| 81 | " | " | NHCH$_2$—C$_6$H$_4$(Cl) | " | 171–173 |
| 82 | " | C$_2$H$_5$ | NHOCH$_2$—C$_6$H$_4$—C$_4$H$_9^t$ | Cl | n$_D^{25}$ 1.5407 |
| 83 | " | CH$_3$ | NHCH$_2$—C$_6$H$_4$—C$_4$H$_9^t$ | NHCOCH$_3$ | 140–141 |
| 84 | " | " | " | NHCOCH$_2$Cl | 172–173 |
| 85 | " | " | " | NHCOOC$_2$H$_5$ | 124–125 |
| 86 | " | " | NHCH$_2$—C$_6$H$_4$—C$_4$H$_9^t$ | NHCO—C$_6$H$_5$ | 169–171 |
| 87 | " | C$_2$H$_5$ | " | H | 81–83 |
| 88 | " | " | " | Br | 93–95 |
| 89 | " | " | NHCH$_2$—C$_6$H$_4$—C$_4$H$_9^n$ | " | 37–38 |
| 90 | " | " | NHCH$_2$—C$_6$H$_3$(C$_4$H$_9^t$)(OCH$_3$) | " | 115–117 |
| 91 | " | " | NHCH$_2$—C$_6$H$_4$—CH$_3$ | Cl | 114–115 |

TABLE 1-continued

Structure:
$R^2$ and X on pyrazole ring positions, N-N with $R^1$, C(=O)-$R^4$ substituent.

| Compound No. | $R^1$ | $R^2$ | $R^4$ | X | $n_D$ (Refractive index) m.p (Melting point) °C. |
|---|---|---|---|---|---|
| 92 | " | " | NHCH$_2$-C$_6$H$_4$-CF$_3$ | " | 106–108 |
| 93 | " | " | NHCH$_2$-C$_6$H$_4$-C$_2$H$_5$ | " | 101–102 |
| 94 | " | " | NHCH$_2$-C$_6$H$_4$-C$_3$H$_7{}^n$ | " | 85–87 |
| 95 | " | " | NHCH$_2$-C$_6$H$_4$-C$_3$H$_7{}^n$ (ortho) | " | 78–80 |
| 96 | " | " | NHCH$_2$-C$_6$H$_4$-C$_3$H$_7{}^i$ | " | 66–67 |
| 97 | " | C$_2$H$_5$ | NHCH$_2$-C$_6$H$_4$-C$_4$H$_9{}^n$ | " | 78–79 |
| 98 | " | " | NHCH$_2$-C$_6$H$_4$-C$_4$H$_9{}^i$ | " | 67–68 |
| 99 | " | " | NHCH$_2$-C$_6$H$_4$-C$_4$H$_9{}^{sec}$ | " | $n_D^{24}$ 1.5462 |
| 100 | " | " | NHCH$_2$-C$_6$H$_4$-C$_5$H$_{11}{}^n$ | " | 69–71 |
| 101 | " | " | NHCH$_2$-C$_6$H$_4$-C(CH$_3$)$_2$C$_2$H$_5$ | " | 74–76 |
| 102 | " | " | NHCH$_2$-C$_6$H$_4$-C$_6$H$_{13}{}^n$ | " | 47–48 |

TABLE 1-continued

[Structure: pyrazole with R² at 3-position, X at 4-position, R¹ on N1, and C(=O)R⁴ at 5-position]

| Compound No. | R¹ | R² | R⁴ | X | $n_D$ (Refractive index) m.p (Melting point) °C. |
|---|---|---|---|---|---|
| 103 | " | " | NHCH₂–C₆H₄–C₈H₁₇ⁿ | " | 73–74 |
| 104 | " | " | NHCH₂–C₆H₄–cyclopropyl | " | 88–91 |
| 105 | " | " | NHCH₂–C₆H₄–CO₂C₂H₅ | " | 106–107 |
| 106 | " | " | NHCH₂–C₆H₄–COOC₃H₇ⁱ | " | 107–108 |
| 107 | " | " | NHCH₂–C₆H₄–CONHC₃H₇ⁿ | " | 158–159 |
| 108 | " | " | NHCH₂–C₆H₄–CON(CH₃)₂ | " | 97–98 |
| 109 | " | " | NHCH₂–C₆H₄–CN | " | 166–167 |
| 110 | " | " | NHCH₂–C₆H₄–CH₂OC₂H₅ | " | 72–73 |
| 111 | " | " | NHCH₂–C₆H₅ | " | 89–90 |
| 112 | " | " | NHCH₂–C₆H₄–OCH₃ | " | 75–77 |
| 113 | " | " | NHCH₂–C₆H₃(OC₃H₇ⁱ)(Cl) | " | 137–138 |

TABLE 1-continued $$\underset{R^1}{\underset{|}{N-N}}\overset{R^2}{\underset{\underset{O}{\parallel}{C-R^4}}{\rangle}}\overset{X}{}$$

| Compound No. | R[1] | R[2] | R[4] | X | $n_D$ (Refractive index) m.p (Melting point) °C. |
|---|---|---|---|---|---|
| 114 | " | " | NHCH₂–⟨C₆H₃(OCH₃)⟩–C₄H₉$^t$ | " | 84–85 |
| 115 | " | " | NHCH₂CH₂–⟨C₆H₄⟩–C₄H₉$^t$ | " | $n_D^{25}$ 1.5411 |
| 116 | " | " | OCH₂–⟨C₆H₄⟩–C₄H₉$^t$ | " | $n_D^{25}$ 1.5362 |
| 117 | " | " | OCH₂–⟨C₆H₄⟩–C₄H₉$^n$ | " | $n_D^{25}$ 1.5347 |
| 118 | " | " | NHCH₂–⟨C₆H₄⟩–CH₃ | CH₃ | 133–134 |
| 119 | " | " | NHCH₂–⟨C₆H₄⟩–CF₃ | " | 130–131 |
| 120 | " | " | NHCH₂–⟨C₆H₄⟩–C₃H₇$^i$ | " | 83–85 |
| 121 | " | " | NHCH₂–⟨C₆H₄⟩–C₄H₉$^n$ | " | 81–82 |
| 122 | " | " | NHCH₂–⟨C₆H₄⟩–C₄H₉$^t$ | " | 81–82 |
| 123 | " | C₃H₇$^n$ | " | Br | 82–83 |
| 124 | " | " | " | Cl | 70–71 |
| 125 | " | C₂H₅ | NHCH₂–⟨C₆H₄⟩–OCHF₂ | " | 88–90 |
| 126 | " | " | NHCH₂–⟨C₆H₄⟩–OC₂H₅ | " | 100–101 |

TABLE 1-continued

Structure:
$R^2$ and $X$ on pyrazole ring; N-N with $R^1$; C(=O)-$R^4$

| Compound No. | $R^1$ | $R^2$ | $R^4$ | X | $n_D$ (Refractive index) m.p (Melting point) °C. |
|---|---|---|---|---|---|
| 127 | " | " | NHCH$_2$-C$_6$H$_4$-OCH$_2$CF$_3$ (4-) | " | 104–105 |
| 128 | " | " | NHCH$_2$-C$_6$H$_4$-OC$_3$H$_7{}^n$ (4-) | " | 82–83 |
| 129 | " | " | NHCH$_2$-C$_6$H$_4$-OC$_3$H$_7{}^i$ (4-) | " | 65–66 |
| 130 | " | " | NHCH$_2$-C$_6$H$_4$-OC$_4$H$_9{}^n$ (4-) | " | 70–71 |
| 131 | " | " | NHCH$_2$-C$_6$H$_4$-Br (4-) | " | 118–119 |
| 132 | " | " | NHCH$_2$-C$_6$H$_4$-NO$_2$ (4-) | " | 139–140 |
| 133 | " | " | NHCH$_2$-C$_6$H$_4$-NH$_2$ (4-) | " | 130–132 |
| 134 | " | " | NHCH$_2$-C$_6$H$_4$-NHC$_3$H$_7{}^n$ (4-) | " | 65–67 |
| 135 | " | " | NHCH$_2$-C$_6$H$_4$-SCH$_3$ (4-) | " | 85–86 |
| 136 | " | " | NHCH$_2$-C$_6$H$_4$-S(O)CH$_3$ (4-) | " | 74–76 |
| 137 | " | " | NHCH$_2$-C$_6$H$_4$-S(O)$_2$CH$_3$ (4-) | " | 138–139 |
| 138 | " | C$_3$H$_7{}^n$ | NHCH$_2$-C$_6$H$_4$-C$_4$H$_9{}^n$ (4-) | " | 64–66 |

TABLE 1-continued $$\underset{\underset{R^1}{N-N}}{\overset{R^2}{\underset{\|}{\bigwedge}}}\overset{X}{\underset{\overset{\|}{O}}{\bigwedge}}R^4$$

| Compound No. | $R^1$ | $R^2$ | $R^4$ | X | $n_D$ (Refractive index) m.p (Melting point) °C. |
|---|---|---|---|---|---|
| 139 | " | △ | " | " | 74–75 |
| 140 | " | " | NHCH$_2$–C$_6$H$_4$–C$_4$H$_9{}^t$ | " | 92–93 |
| 141 | CHF$_2$ | CH$_3$ | NHCH$_2$–C$_6$H$_4$–C$_4$H$_9{}^t$ | " | 111–113 |
| 142 | " | " | NHCH(CH$_3$)–C$_6$H$_4$–C$_4$H$_9{}^t$ | " | 109–111 |
| 143 | C$_2$H$_5$ | C$_2$H$_5$ | NHCH$_2$–C$_6$H$_4$–C$_4$H$_9{}^t$ | " | 67–68 |
| 144 | CH$_3$ | " | NHCH$_2$–C$_6$H$_4$–COOC$_2$H$_4$–OC$_2$H$_5$ | " | 101–103 |
| 145 | " | " | NHCH$_2$–C$_6$H$_4$–COO–C$_6$H$_{11}$ | " | 88–89 |
| 146 | " | " | NHCH$_2$–C$_6$H$_4$–CON(C$_2$H$_5$)$_2$ | " | 118–119 |
| 147 | " | " | NHCH$_2$–C$_6$H$_4$–CON(piperidine) | " | 102–103 |
| 148 | " | " | NHCH$_2$–C$_6$H$_4$–CON(morpholine) | " | 130.5–131.5 |
| 149 | " | " | NHCH$_2$–C$_6$H$_4$–C$_4$H$_9{}^t$ | NHC$_3$H$_7{}^n$ | $n_D{}^{25}$ 1.5395 |
| 150 | " | " | " | N(C$_3$H$_7{}^n$)$_2$ | 47–48 |

TABLE 1-continued
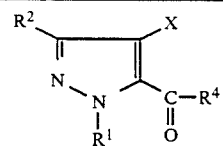
| Compound No. | R¹ | R² | R⁴ | X | $n_D$ (Refractive index) m.p (Melting point) °C. |
|---|---|---|---|---|---|
| 151 | " | ClCH₂ | " | CH₃ | 99–100 |
| 152 | " | CH₃CH(Cl) | " | Cl | $n_D^{25}$ 1.5578 |
TABLE 2
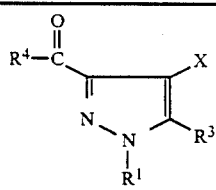
| Compound No. | R¹ | R³ | R⁴ | X | Melting point (°C.) |
|---|---|---|---|---|---|
| 153 | CH₃ | CH₃ | NH—CH(CH₃)—C₆H₅ | H | 111.0–113.0 |
| 154 | " | " | NH—C(CH₃)₂—C₆H₅ | " | 77.5–79.5 |
| 155 | " | " | NH—CH(CH₃)—C₆H₅ | Br | 117.5–118.5 |
| 156 | " | " | NH—C(CH₃)₂—C₆H₅ | " | 76.5–78.0 |
| 157 | " | " | NH—CH(CH₃)—C₆H₄—C₄H₉ᵗ | " | amorphous solid |
| 158 | " | " | NH—CH₂—C₆H₄—C₄H₉ᵗ | CH₃ | 150.0–151.0 |
| 159 | C₄H₉ᵗ | " | NH—CH(CH₃)—C₆H₄—C₄H₉ᵗ | Br | 106.5–107.5 |
| Compound No. | R¹ | R² | R⁴ | X | Melting point (°C.) |
|---|---|---|---|---|---|

TABLE 2-continued

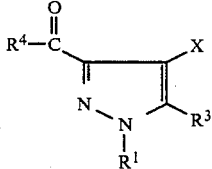

| | | | | | |
|---|---|---|---|---|---|
| 160 | 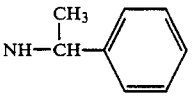 | CH₃ | NH—CH(CH₃)—Ph | Br | 89.0–90.0 |
| 161 | " | " | NH—C(CH₃)₂—Ph | " | 147.0–149.0 |
| 162 | " | " | NH—CH₂—C₆H₄—C₄H₉ᵗ | " | 116.0–116.5 |
| 163 | CH₃ | C₄H₉ᵗ | " | Cl | 136.5–138.5 |
| 164 | " | C₂H₅ | " | " | 217–218 |
| 165 | CHF₂ | CH₃ | " | " | 128–129 |

TABLE 3

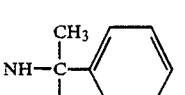

| Compound No. | R¹ | R² | R⁴ | X | Melting point (°C.) |
|---|---|---|---|---|---|
| 166 | CH₃ | CH₃ | NHCH₂—C₆H₄—C₄H₉ᵗ | Br | 117–119 |
| 167 | " | " | " | Cl | 121–123 |
| 168 | " | C₂H₅ | " | " | 93–95 |

Formulation examples of the compound according to the present invention are shown below, in which "parts" and "%" means "parts by weight" and "% by weight" respectively.

FORMULATION EXAMPLE 1

Wettable Powder

A wettable powder containing 40% of the effective ingredient was prepared by uniformly mixing and pulverizing 20 parts of each of the compounds according to the present invention shown in Tables 1 to 3, 20 parts of Carplex #80 (trademark, manufactured by Shionogi Seiyaku Co.), 55 parts of N,N Kaolin Clay (trademark, manufactured by Tsuchiya Kaolin Co.), and 5 parts of Sorpol 8070, a higher alcohol sulfuric ester type surface active agent (trademark, manufactured by Toho Kagaku Co.).

FORMULATION EXAMPLE 2

Dust

A dust containing 2% effective ingredient was prepared by uniformly mixing and pulverizing 2 parts of each of the compounds according to the present invention shown in Tables 1 to 3, 93 parts of clay (manufactured by Nippon Talc Co.) and 5 parts of white carbon.

FORMULATION EXAMPLE 3

Emulsifiable Concentrate

An emulsifiable concentrate containing 20% of the effective ingredients was prepared by dissolving 20 parts of each of the compounds according to the present invention shown in Tables 1 to 3 into a mixed solvent comprising 35 parts of xylene and 30 parts of dimethylformamide and adding thereto 15 parts of Sorpol 3005X, a polyoxyethylene type surface active agent (trademark, manufactured by Toho Kagaku Co.).

FORMULATION EXAMPLE 4

Flowable Agent

A stable flowable agent containing 30% of the effective ingredients was prepared by mixing and dispersing 30 parts of the compound according to the present invention shown in Tables 1 to 3 and a previously prepared mixture of 8 parts of ethylene glycol, 5 parts of Sorpol AC 3032 (trademark, manufactured by Toho Kagaku Co.) and 0.1 parts of xanthene gum into 56.9 parts of water, and then pulverizing the slurry-like mixture in the wet process in a DYNO-MILL (manufactured by Shinmaru Enterprises Co.).

TEST EXAMPLE 1

Effect against adult *Tetranychus urticae*

Ten female adult *Tetranychus urticae* were put to a leaf disc (2 cm diameter) of a kidney bean leaf. Then, 5 ml of a solution, prepared by diluting each of insecticidal and miticidal compositions of the present invention formulated in accordance with the preparation of Formulation Example 1 with water to a predetermined concentration, was scattered by using a rotary type scattering tower (manufactured by Mizuho Rika Co.). Test was repeated twice for one concentration.

24 hours after the treatment, the number of live and dead larvae were investigated and the miticidal activity (%) was determined by the following equation.

$$\text{Miticidal Activity (\%)} = \frac{\text{Number of dead larvae}}{\text{Number of treated larvae}} \times 100$$

The results are shown in Table 4.

TEST EXAMPLE 2

Effect against eggs of *Tetranychus urticae*

Five female adult *Tetranychus urticae* were put to a leaf disc (2 cm diameter) of a kidney bean leaf. The mites were allowed to oviposit on the leaf disc for 20 hours after putting and then the adult females mites were removed. Then, 5 ml of a solution prepared by diluting each of insecticidal and miticidal compositions of the present invention formulated in accordance with the preparation of Formulation Example 1 with water to a predetermined concentration was scattered by using a rotary type scattering tower (manufactured by Mizuho Rika Co.). Test was repeated twice for one concentration.

The number of unhatched eggs and the number of hatched larvae were investigated 5 days after the treatment to determine the ovicidal activity (%) by the following equation.

$$\text{Ovicidal Activity (\%)} = \frac{\text{Number of unhatched eggs}}{\text{Number of unhatched eggs + Number of hatched eggs}}$$

The results are shown in Table 4.

TABLE 4

| Compound No. | Concentration (ppm) | Miticidal Activity (%) | Ovicidal Activity (%) |
|---|---|---|---|
| 1 | 500 | 100 | 100 |
| 13 | " | " | " |
| 14 | " | " | " |
| 19 | " | " | " |
| 30 | " | " | " |
| 33 | " | " | " |
| 34 | " | " | " |
| 35 | " | " | " |
| 36 | " | " | " |
| 41 | " | " | " |
| 51 | " | " | " |
| 52 | " | " | " |
| 59 | " | " | " |
| 60 | " | " | " |
| 61 | " | " | " |
| 66 | " | " | " |
| 72 | " | " | " |
| 73 | " | " | " |
| 74 | " | " | " |
| 75 | 500 | 100 | 100 |
| 77 | " | " | " |
| 79 | " | " | " |
| 87 | " | " | " |
| 88 | " | " | " |
| 89 | " | " | " |
| 90 | " | " | " |
| 93 | " | " | " |
| 94 | " | " | " |
| 96 | " | " | " |
| 97 | " | " | " |
| 98 | " | " | " |
| 99 | " | " | " |
| 100 | " | " | " |
| 101 | " | " | " |
| 102 | " | " | " |
| 103 | " | " | " |
| 106 | " | " | " |
| 107 | " | " | " |
| 108 | " | " | " |
| 110 | " | " | " |
| 114 | 500 | 100 | 100 |
| 117 | " | " | " |
| 120 | " | " | " |
| 121 | " | " | " |
| 122 | " | " | " |
| 123 | " | " | " |
| 124 | " | " | " |
| 125 | " | " | " |
| 127 | " | " | " |
| 128 | " | " | " |
| 129 | " | " | " |
| 130 | " | " | " |
| 134 | " | " | " |
| 138 | " | " | " |
| 139 | " | " | " |
| 146 | " | " | " |
| 149 | " | " | " |
| 151 | " | " | " |
| 152 | " | " | " |
| 166 | " | " | " |
| 168 | " | " | " |

TEST EXAMPLE 3

Effect against larvae of *Nilaparvata lugens*

Germinated seedlings of rice plant were set to a glass cylinder (3 cm diameter, 17 cm length) and five larvae of fourth instar of *Nilaparvata lugens* were put to them. Then, each of the insecticidal and miticidal compositions according to the present invention formulated in accordance with the preparation of Formulation Example 3 was diluted with water and scattered by 0.5 ml using a scattering tower (manufactured by Mizuho Rika Co.). Test was repeated four times for one centration. Twenty-four hours after the treatment, the number of dead larvae was examined to determine the mortality (%). The results are shown in Table 5.

TEST EXAMPLE 4

Effect against larvae of *Plutella xylostella*

Slices of cabbage leaves (5×5 cm) were immersed for one minute in a water-diluted solution of each of the insecticidal and miticidal compositions of the present invention formulated in accordance with the preparation of Formulation Example 1. They were air-dried after immersion and placed in a plastic cup (7 cm diameter), to which five larvae of third instar of *Plutella xylostella* were put. Test was repeated twice for one concentration.

Two days after putting, the number of dead larvae was examined to determine the mortality (%). The results are shown in Table 5.

TABLE 5

| Compound No. | Concentration (ppm) | Mortality (%) | |
|---|---|---|---|
| | | *Nilaparvata lugens* | *Plutella xylostella* |
| 1 | 500 | 100 | 100 |
| 13 | " | " | " |
| 14 | " | " | " |
| 19 | " | " | " |
| 30 | " | " | " |
| 33 | " | " | " |
| 34 | " | " | " |
| 35 | " | " | " |
| 36 | " | " | " |
| 41 | " | " | " |
| 51 | " | " | " |
| 52 | " | " | " |
| 59 | " | " | " |
| 60 | " | " | " |
| 61 | " | " | " |
| 66 | " | " | " |
| 72 | " | " | " |
| 73 | " | " | " |
| 74 | 500 | 100 | 100 |
| 75 | " | " | " |
| 77 | " | " | " |
| 79 | " | " | " |
| 87 | " | " | " |
| 88 | " | " | " |
| 89 | " | " | " |
| 90 | " | " | " |
| 93 | " | " | " |
| 94 | " | " | " |
| 96 | " | " | " |
| 97 | " | " | " |
| 98 | " | " | " |
| 99 | " | " | " |
| 100 | " | " | " |
| 101 | " | " | " |
| 102 | " | " | " |
| 103 | " | " | " |
| 106 | " | " | " |
| 107 | " | " | " |
| 108 | " | " | " |
| 110 | " | " | " |
| 114 | " | " | " |
| 117 | 500 | 100 | 100 |
| 120 | " | " | " |
| 121 | " | " | " |
| 122 | " | " | " |
| 123 | " | " | " |
| 124 | " | " | " |
| 125 | " | " | " |
| 127 | " | " | " |
| 128 | " | " | " |
| 129 | " | " | " |
| 130 | " | " | " |
| 134 | " | " | " |
| 138 | " | " | " |
| 139 | " | " | " |
| 146 | " | " | " |
| 149 | " | " | " |
| 151 | " | " | " |
| 152 | " | " | " |
| 166 | " | " | " |
| 168 | " | " | " |

TEST EXAMPLE 5

Effect against nymphae of Tick (*Ornithodoros moubata*)

To a glass laboratory dish (9 cm diameter), 1 ml of 200 ppm acetone solution of the compound of the present invention shown in Tables 1 to 3 (corresponding to 200 g of the compound) was added dropwise. A film of the compound was formed inside of the glass laboratory dish by air-drying. Into the thus treated glass dish, ten nymphae of third instar of *Ornithodoros moubata*, a species belonging to Tick, were put.

Ten days after putting, the number of dead nymphae was examined to determine the mortality (%). The test was repeated twice for one concentration.

The results are shown in Table 6.

TABLE 6

| Compound No. | Mortality (%) |
|---|---|
| 13 | 100 |
| 19 | " |
| 36 | " |
| 39 | " |
| 51 | " |
| 72 | " |
| 77 | " |
| 97 | " |
| 103 | " |
| 108 | " |
| 125 | " |
| 128 | " |
| 134 | " |
| 151 | " |
| 168 | " |

What is claimed is:
1. A pyrazole derivative represented by the following formula (I)

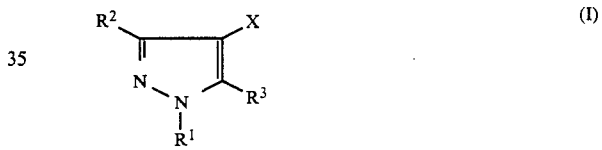

wherein $R^1$ represents $C_1$–$C_4$ alkyl group, $C_1$–$C_4$ haloalkyl group, phenyl group or benzyl group; one of $R^2$ and $R^3$ represents

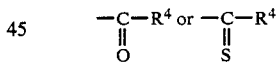

wherein $R^4$ represents

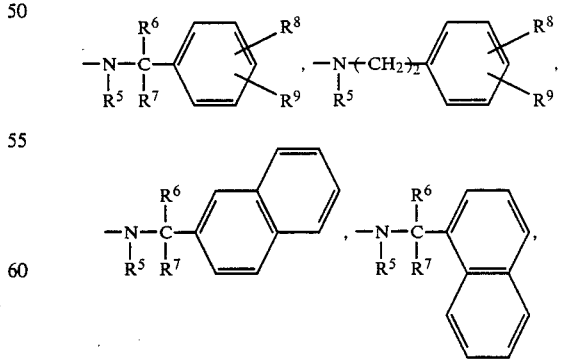

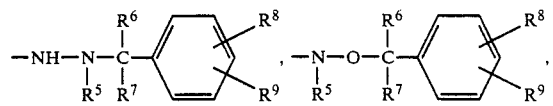

-continued

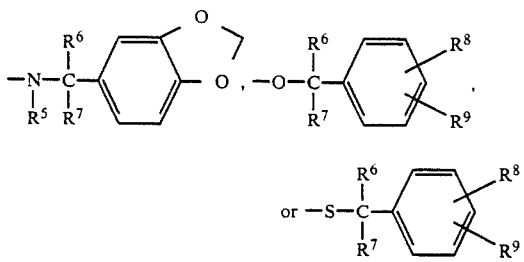

wherein $R^5$, $R^6$ and $R^7$ represent respectively hydrogen atom, $C_1$-$C_4$ alkyl group or phenyl group, $R^8$ and $R^9$ represent respectively hydrogen atom, halogen atom, $C_1$-$C_8$ alkyl group, $C_3$-$C_5$ alkenyl group, $C_3$-$C_5$ alkynyl group, $C_3$-$C_6$ cycloalkyl group, $C_2$-$C_4$ alkoxyalkyl group, $C_1$-$C_4$ alkoxy group, $C_1$-$C_4$ haloalkoxy group, nitro group, trifluoromethyl group, phenyl group, benzyl group, phenoxy group, benzyloxy group, amino group, $C_1$-$C_4$ alkylamino group, $C_2$-$C_8$ dialkylamino group, cyano group, carboxyl group, $C_2$-$C_5$ alkoxycarbonyl group, $C_4$-$C_7$ cycloalkoxycarbonyl group, $C_3$-$C_9$ alkoxyalkoxycarbonyl group, $C_2$-$C_6$ alkylaminocarbonyl group, $C_3$-$C_{11}$ dialkylaminocarbonyl group, piperidinocarbonyl group, morpholinocarbonyl group, trimethylsilyl group, $C_1$-$C_4$ alkylthio group, $C_1$-$C_4$ alkylsulfinyl group, or $C_1$-$C_4$ alkylsulfonyl group; the other of $R^2$ and $R^3$ represents hydrogen atom, $C_1$-$C_4$ alkyl group, $C_1$-$C_4$ haloalkyl group, $C_3$-$C_6$ cycloalkyl group or phenyl group; X represents hydrogen atom, halogen atom, $C_1$-$C_4$ alkyl group, nitro group, cyano group, $C_1$-$C_5$ alkylamino group, $C_2$-$C_{10}$ dialkylamino group and $C_2$-$C_7$ acylamino group.

2. The pyrazole derivative according to claim 1, wherein $R^1$ is $C_1$-$C_4$ alkyl group, phenyl group or benzyl group; $R^2$ is hydrogen atom, $C_1$-$C_4$ alkyl group, $C_3$-$C_8$ cycloalkyl group or $C_1C_4$ haloalkyl group; $R^3$ is

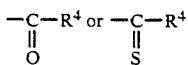

wherein $R^4$ is

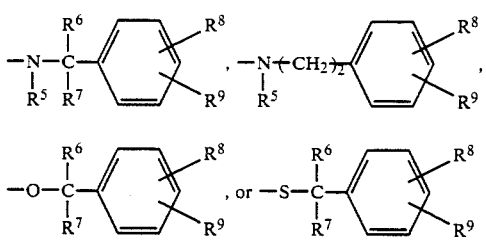

wherein $R^5$, $R^6$, $R^7$, $R^9$ have the same meanings as defined in claim 1; and X is hydrogen atom, halogen atom, $C_1$-$C_4$ alkyl group, cyano group or $C_1$-$C_4$ alkylamino group.

3. The pyrazole derivative according to claim 2, wherein $R^1$ is $C_1$-$C_4$ alkyl group, and $R^5$ and $R^9$ are hydrogen atoms.

4. An insecticidal and miticidal composition comprising, as the effective ingredient, an insecticidally and miticidally effective amount of a pyrazole derivative represented by the following formula (I)

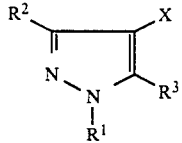

wherein $R^1$ represents $C_1$-$C_4$ alkyl group, $C_1$-$C_4$ haloalkyl group, phenyl group or benzyl group; one of $R^2$ and $R^3$ represents

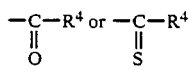

wherein $R^4$ represents

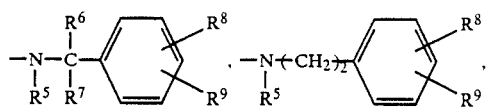

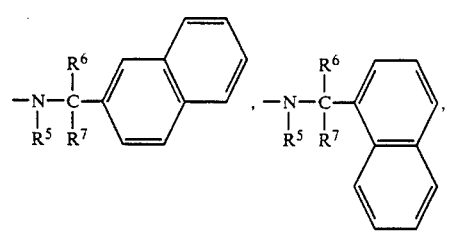

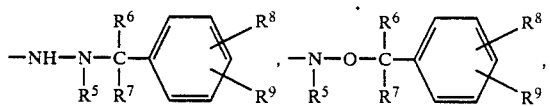

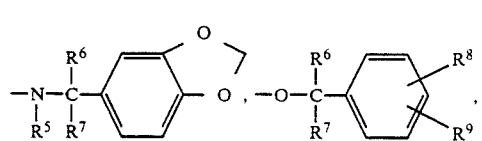

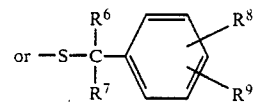

wherein $R^5$, $R^6$ and $R^7$ represent respectively hydrogen atom, $C_1$-$C_4$ alkyl group or phenyl group, $R^8$ and $R^9$ represent respectively hydrogen atom, halogen atom, $C_1$-$C_8$ alkyl group, $C_3$-$C_5$ alkenyl group, $C_3$-$C_5$ alkynyl group, $C_3$-$C_6$ cycloalkyl group, $C_2$-$C_4$ alkoxyalkyl group, $C_1$-$C_4$ alkoxy group, $C_1$-$C_4$ haloalkoxy group, nitro group, trifluorometbyl group, phenyl group, benzyl group, phenoxy group, benzyloxy group, amino group, $C_1$-$C_4$ alkylamino group, $C_2$-$C_8$ dialkylamino group, cyano group, carboxyl group, $C_2$-$C_5$ alkoxycarbonyl group, $C_4$-$C_7$ cycloalkoxycarbonyl group, $C_3$-$C_9$ alkoxyalkoxycarbonyl group, $C_2$-$C_6$ alkylaminocarbonyl group, $C_3$-$C_{11}$ dialkylaminocarbonyl group, piperidinocarbonyl group, morpholinocarbonyl group, trimethylsilyl group, $C_1$-$C_4$ alkylthio group, $C_1$-$C_4$ alkylsulfinyl group, or $C_1$-$C_4$ alkylsulfonyl group; the other of $R^2$ and $R^3$ represents hydrogen atom, $C_1$-$C_4$ alkyl group, $C_1$-$C_4$ haloalkyl group, $C_3$-$C_6$ cycloalkyl group or phenyl group; X represents hydrogen atom, halogen atom, $C_1$-$C_4$ alkyl group, nitro group, cyano group, $C_1$-$C_5$ alkylamino group, $C_2$-$C_{10}$ dialkylamino group and $C_2$-$C_7$ acylamino group; and insecticidally and miticidally acceptable adjuvant(s).

5. The insecticidal and miticidal composition according to claim 4, wherein $R^1$ is $C_1$-$C_4$ alkyl group, phenyl group or benzyl group; $R^2$ is hydrogen atom, $C_1$-$C_4$ alkyl group, $C_3$-$C_8$ cycloalkyl group or $C_1$-$C_4$ haloalkyl group; $R^3$ is

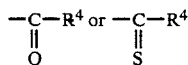

wherein $R^4$ is

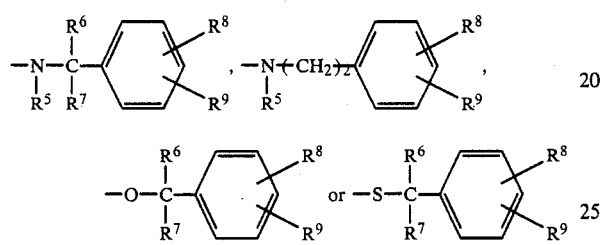

wherein $R^5$, $R^6$, $R^7$, $R^8$ and $R^9$ have the same meanings as defined in claim 1; and X is hydrogen atom, halogen atom, $C_1$-$C_4$ alkyl group, cyano group or $C_1$-$C_4$ alkylamino group.

6. The insecticidal and miticidal composition according to claim 5, wherein $R^1$ is $C_1$-$C_4$ alkyl group, and $R^5$ and $R^9$ are hydrogen atoms.

7. A method of controlling insects and mites which comprises applying an insecticidally and miticidally effective amount of a pyrazole derivative represented by the following formula (1)

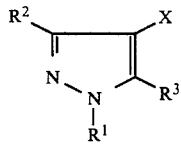

wherein $R^1$ represents $C_1$-$C_4$ alkyl group, $C_1$-$C_4$ haloalkyl group, phenyl group or benzyl group; one of $R^2$ and $R^3$ represents

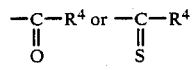

wherein $R^4$ represents

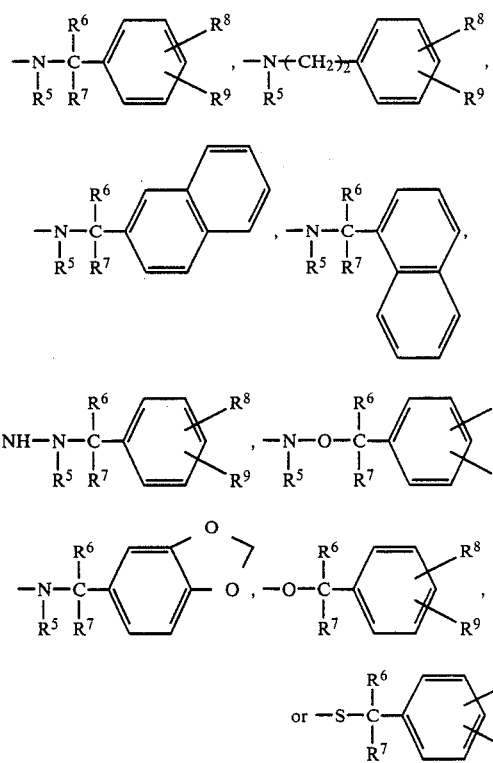

wherein $R^5$, $R^6$ and $R^7$ represent respectively hydrogen atom, $C_1$-$C_4$ alkyl group or phenyl group, $R^8$ and $R^9$ represent respectively hydrogen atom, halogen atom, $C_1$-$C_8$ alkyl group, $C_3$-$C_5$ alkenyl group, $C_3$-$C_5$ alkynyl group, $C_3$-$C_6$ cycloalkyl group, $C_2$-$C_4$ alkoxyalkyl group, $C_1$-$C_4$ alkoxy group, $C_1$-$C_4$ haloalkoxy group, nitro group, trifluoromethyl group, phenyl group, benzyl group, phenoxy group, benzyloxy group, amino group, $C_1$-$C_4$ alkylamino group, $C_2$-$C_8$ dialkylamino group, cyano group, carboxyl group, $C_2$-$C_5$ alkoxycarbonyl group, $C_4$-$C_7$ cycloalkoxycarbonyl group, $C_3$-$C_9$ alkoxyalkoxycarbonyl group, $C_2$-$C_6$ alkylaminocarbonyl group, $C_3$-$C_{11}$ dialkylaminocarbonyl group, piperidinocarbonyl group, morpholinocarbonyl group, trimethylsilyl group, $C_1$-$C_4$ alkylthio group, $C_1$-$C_4$ alkylsulfinyl group, or $C_1$-$C_4$ alkylsulfonyl group; the other of $R^2$ and $R^3$ represents hydrogen atom, $C_1$-$C_4$ alkyl group, $C_1$-$C_4$ haloalkyl group, $C_3$-$C_6$ cycloalkyl group or phenyl group; X represents hydrogen atom, halogen atom, $C_1$-$C_4$ alkyl group, nitro group, cyano group, $C_1$-$C_5$ alkylamino group, $C_2$-$C_{10}$ dialkylamino group and $C_2$-$C_7$ acylamino group, to eggs or larvae of said insects or mites.

* * * * *